United States Patent [19]
McCarthy

[11] 3,935,729
[45] Feb. 3, 1976

[54] GAP FILLER FOR RHEOMETER

[75] Inventor: Robert V. McCarthy, Columbia, Pa.

[73] Assignee: Armstrong Cork Company, Lancaster, Pa.

[22] Filed: Jan. 27, 1975

[21] Appl. No.: 544,654

[52] U.S. Cl. ................................................. 73/60
[51] Int. Cl.² ....................................... G01N 11/10
[58] Field of Search .............................. 73/59, 60

[56] References Cited
UNITED STATES PATENTS
2,812,656  11/1957  Merrill ............................... 73/60

*Primary Examiner*—Richard C. Queisser
*Assistant Examiner*—Joseph W. Roskos

[57] ABSTRACT

A coaxial cylinder rheometer having a very small (less than 0.020 inches [0.0508 cm]) gap between the concentric cylinders and being capable of charging highly viscous (greater than 100,000 poise) and/or thermally sensitive materials, e.g., Polyvinyl Chloride, Polyurethane, etc., into this gap for testing. The inner cylinder, rotor, comprises a single element which can be driven axially and rotationally. The outer cylinder, stator, comprises an upper part having a projection-like ring on its lower surface and a lower part having a trough-like ring in its upper surface. The two parts are fastened together with mating screw threads on each part. The material to be tested is deposited in the trough-like ring in the lower part and the two parts are screwed together into an operational position wherein simultaneously the projection-like ring moves into the trough-like ring extruding the flowable material therebetween into the gap between the coaxial cylinders and the bottom and top edges of the inner surfaces of the upper and lower parts, respectively, come together to form a complete and uninterrupted outer cylinder inner surface.

11 Claims, 3 Drawing Figures

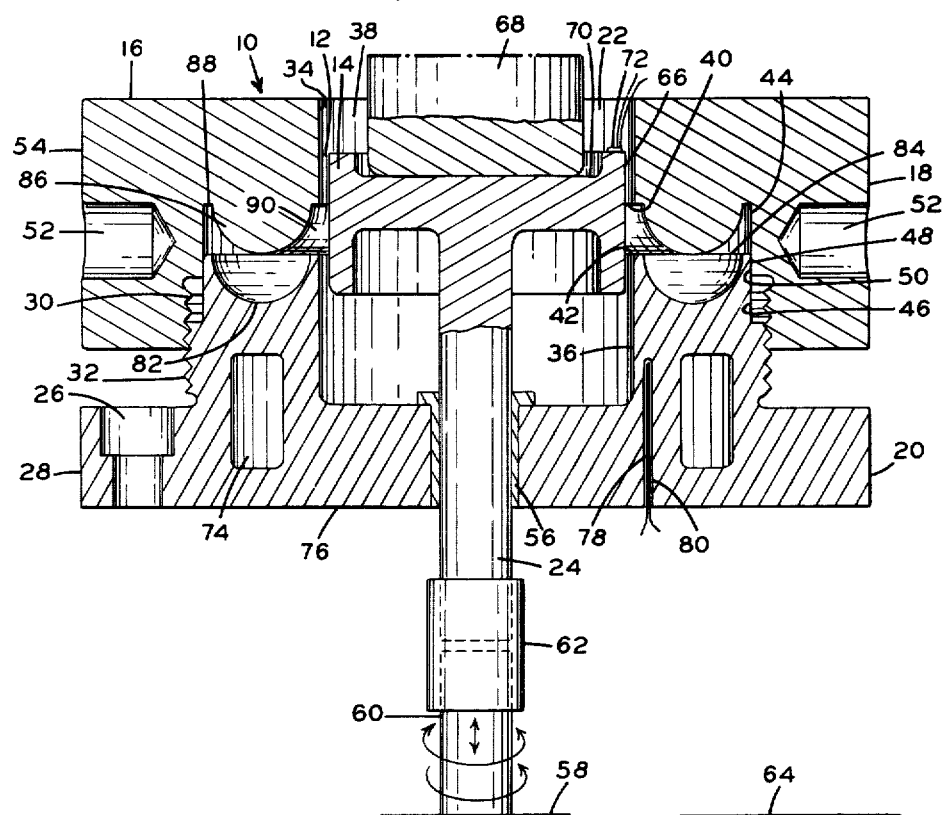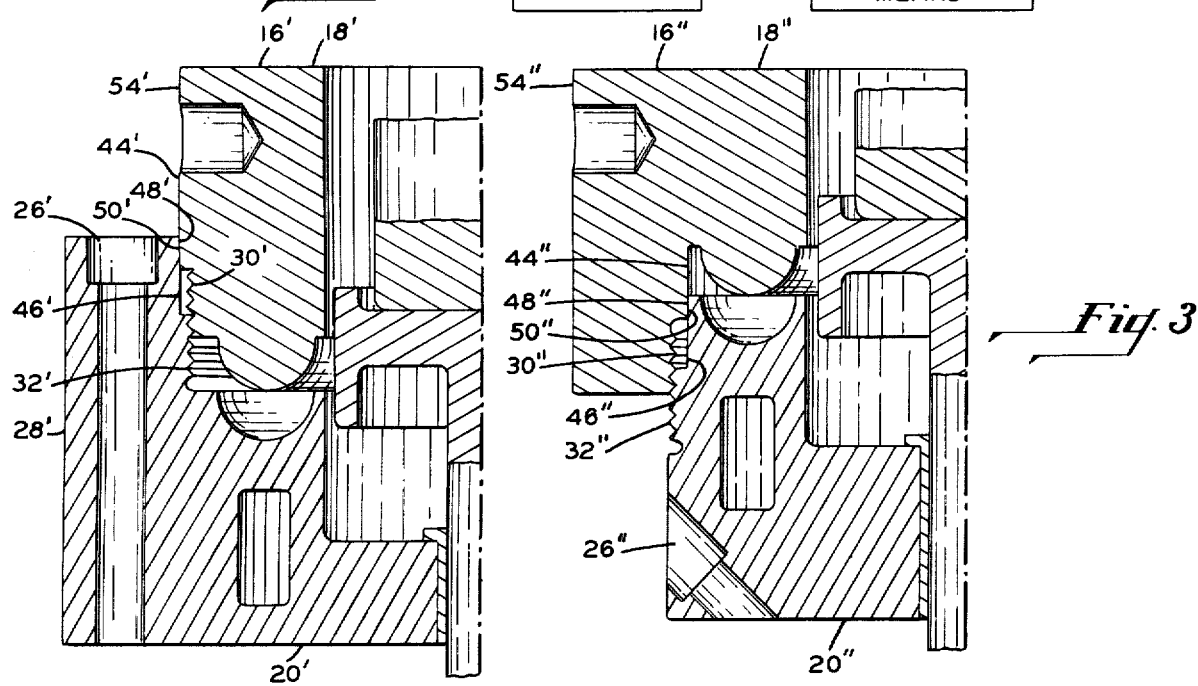

GAP FILLER FOR RHEOMETER

BACKGROUND OF THE INVENTION

1. Field of the Invention

This invention relates to a coaxial cylinder rheometer for testing the rheological properties of highly viscous and/or thermally sensitive materials. More particularly, this invention concerns a coaxial cylinder rheometer having a very small (less than 0.020 inches [0.0508 cm]) gap between the concentric cylinders and being capable of charging highly viscous (greater than 100,000 poise) and/or thermally sensitive materials, e.g., Polyvinyl Chloride, Polyurethane, etc., into the gap for testing.

2. Description of the Prior Art

U.S. Pat. No. 2,812,656 discloses a coaxial cylinder viscometer in which the fluid to be tested is forced into the gap between the cylinders by means of a syringe through a hole and/or holes in the outer cylinder. The patent teaches that a viscometer constructed according to its disclosure has investigated viscosities up to 9,000 centipoises (90 poise) although indicating that this upper limit does not necessarily represent the practical limit of the viscometer. Said patent specifically notes that one of five potential deviations may be caused by the presence of a hole or holes in the outer cylindrical surface of said viscometer. This specific problem is solved by Applicant's invention since the two parts of the outer cylinder have their inner surfaces axially aligned and come into contact to complete an uninterrupted inner surface of this outer cylinder when in its operational position. Also, said patent teaches introduction of the material to be tested into the gap between the cylinders from one point or one vertical location only around the entire circumference of said gap. This may cause the gap to be filled ununiformly and may tend to cause eccentricity of the outer cylinder and inner cylinder. Applicant's invention overcomes these problems by extruding the material into the gap between the cylinders around the entire circumference of the gap. Therefore, the gap is filled uniformly by a force system which tends to maintain concentricity of the outer cylinder and inner cylinder and may actually tend to correct for any eccentricity of the outer cylinder and inner cylinder.

SUMMARY OF THE INVENTION

This invention relates to a coaxial cylinder rheometer comprised of an inner cylinder, rotor, and an outer cylinder, stator, with a very small (less than 0.020 inches [0.0508 cm]) gap between these concentric cylinders and being capable of charging highly viscous (greater than 100,000 poise) and/or thermally sensitive materials, e.g., Polyvinyl Chloride, Polyurethane, etc., into the gap. Conventional means are used for heating the rheometer, for moving the rotor element either axially or rotationally relative said stator element, and for measuring the parameters of movement of the rotor element. The improvement of this rheometer comprises a stator element having two parts, an upper part and a lower part. These two parts are moved together in their operational position and moved apart in their non-operational position.

The upper part has a projection-like ring on a lower surface and the lower part has a trough-like ring in an upper surface. The highly viscous and/or thermally sensitive materials to be tested in this rheometer are deposited in the trough-like ring. The heated rheometer changes the said material from its deposited state to a flowable state. The screw-type connecting means for connecting the upper part to the lower part is such that the inner surface of the upper part is axially aligned with the inner surface of the lower part and the projection-like ring on said lower surface of the upper part is aligned with the trough-like ring on said upper surface of the lower part. As the deposited material changes to a flowable state, the lower part and the upper part are moved together into an operational position wherein simultaneously the projection-like ring moves into the trough-like ring and evenly extrudes the flowable material therebetween into the gap between the rotor and the stator and the bottom edge of the inner surface of the upper part moves into contact with the top edge of the inner surface of the lower part to form a complete and uninterrupted stator inner surface. The system can then be activated immediately for data generation of rheological properties.

A primary object of this invention is to present a mechanism for charging highly viscous (greater than 100,000 poise) and/or thermally sensitive materials, e.g., Polyvinyl Chloride, Polyurethane, etc., into the gap (less than 0.020 inches [0.0508 cm]) of a coaxial cylinder rheometer.

Another object of this invention is to present a mechanism which will distribute the material being charged into the gap uniformly around the gap.

Another object of the invention is to set forth a mechanism capable of charging the material to be tested into the gap of a coaxial cylinder rheometer with said material having a minimum of thermal history before the testing commences.

Another object of the invention is to present a device which when charging material to be tested into the gap of a coaxial cylinder rheometer has a force system tending to maintain concentricity of the rotor and stator or tending to correct for any eccentricity of the rotor and stator. This is important when dealing with a gap of less than 0.020 inches between the rotor and the stator.

Still another object of this invention is to present a coaxial cylinder rheometer capable of charging highly viscous and/or thermally sensitive materials to be tested into the gap and having the outer surface of the rotor and the inner surface of the stator which surfaces comprise the boundary of the gap being uninterrupted surfaces.

A still further object of this invention is to set forth a coaxial cylinder rheometer having a reservoir in which material to be tested is deposited before being charged into the gap and which can accommodate material of low (less than 0.5 gram/cubic centimeter) bulk density.

And yet another object of this invention is to set forth a gap filler for a coaxial cylinder rheometer which permits reservoir pressures in excess of 20,000 PSI (1406.14 kg/cm$^2$) when extruding the material deposited in the reservoir into the gap between the cylinders.

BRIEF DESCRIPTION OF THE DRAWING

FIG. 1 is a vertical cross-sectional view of the rotor and stator elements of the rheometer of this invention.

FIG. 2 is a vertical cross-sectional view of half of the rotor and stator elements of the rheometer of this invention showing a first alternative embodiment of said stator element.

FIG. 3 is a vertical cross-sectional view of half of the rotor and stator elements of the rheomter of this invention showing a second alternative embodiment of said stator element.

DESCRIPTION OF THE PREFERRED EMBODIMENT

The coaxial cylinder rheometer 10 of this invention is capable of charging highly viscous (greater than 100,000 poise) materials and/or thermally sensitive materials, e.g., Polyvinyl Chloride, Polyurethane, etc., into the gap 12 between the outer surface 66 of inner cylinder, rotor, 14 and the inner surface 38 of cavity 22 of outer cylinder, stator, 16 for testing. The gap is less than 0.020 inches (0.0508 cm). The stator 16 has an upper or top part 18 and a lower or bottom part 20. The rotor 14 is concentrically positioned within the cavity 22 of stator 16 by having the shaft 24 of the rotor pass through a hole in the lower part 20 which hole is at the bottom of stator cavity 22.

The lower part 20 of stator 16 is fixedly mounted on any desired mounting surface by any desired conventional fastening means. The fastening means may take the form of a cap screw which would be positioned in the countersunk hole 26 of lower part flange 28. These holes could be evenly spaced around the circumference of flange 28 to provide as many fastening points as are needed to securely mount the lower part 20 on the desired mounting surface. The upper part 18 is connected to lower part 20 by mating screw threads on each part, i.e., screw threads 30 of upper part 18 mate with screw threads 32 of lower part 20.

In order for the inner surface 34 of upper part 18 to be axially aligned with the inner surface 36 of the lower part 20 so that a complete and uninterrupted inner surface 38 of stator cavity 22 is formed when the stator 16 is in its operational position, i.e., when the upper part 18 has been screwed onto the lower part 20 so that the lower edge 40 of the inner surface 34 contacts the upper edge 42 of inner surface 36, the surface 44 on which screw threads 30 are located and the surface 46 on which screw threads 32 are located each have pilot surfaces. Pilot surface 48 is a part of overall surface 44 and pilot surface 50 is a part of overall surface 46. It is these two pilot surfaces 48 and 50 which adjoin one another as the upper part 18 is being screwed onto the lower part 20 and, therefore, assure proper axial alignment of inner surface 34 with inner surface 36.

Top part 18 can be rotated by any convenient conventional means to screw this part onto bottom part 20 thereby axially moving said top and bottom parts into abutting relationship. For example, holes 52 could be spaced around the circumference of the outer surface 54 of the top part 18 so that a conventional spanner wrench could be inserted into any of these holes and used to rotate said top part.

The rotor 14 is the movable part of coaxial cylinder rheometer 10. The shaft 24 of rotor 14 is mounted in bushing 56 to accommodate either axial or rotational movement. The rotor is connected to any conventional drive means 58 through rotor shaft 24, drive means shaft 60, and any conventional shaft coupling means 62. The drive means 58 could be a conventional hydraulic system and provide oscillatory axial movement to the rotor 14. The drive means 58 could also be an electric motor which could provide continuous rotational movement to said rotor. Or the drive means 58 could be an electric motor with conventional bell crank linkage which would provide oscillatory rotational movement to the rotor. The conventional drive means 58 is, therefore, chosen according to the particular mode of operational movement desired for said rotor.

Connected to the conventional drive means 58 is any of a number of conventional movement parameters measuring means 64. The particular movement parameters measuring means 64 employed would be dependent on the particular operational mode in which the rotor is moved. For example, if the rotor 14 were moved in an oscillatory axial movement, the conventional movement parameters measuring means employed would be those used to measure the frequency of oscillation of the rotor, the axial displacement of the rotor, the axial force on the rotor, and the time phase relationship between said force and said displacement. If the rotor 14 were moved in a continuous rotational movement, then the conventional movement parameters measuring means used would be those normally used to measure rotational torque and speed of the rotor. If the rotor 14 were moved in an oscillatory rotational movement, then the parameters necessary to be measured by conventional measuring means would be the frequency of oscillation of the rotor, the angular displacement of the rotor, the torque on the rotor, and the time phase relationship between said torque and said displacement. Many conventional means for measuring these particular parameters are available and are well known in the art.

Before the material to be tested is charged into the rheometer, both the rotor 14 and stator 16 are heated to a desired temperature. This heating and monitoring of the temperature for both the rotor and the stator can be done in any conventional manner. For example, the rotor can be heated by a movable heat sink 68 contacting the upper surface 70 of rotor 14. Heat sink 68 can be moved out of contact with the rotor when the testing of the material charged into gap 12 is initiated. The temperature of rotor 14 can be monitored by a conventional contact thermocouple 72. The stator 16 can be heated by any known conventional rheometer heating means. For example, high temperature oil may be circulated through conduit 74 in the lower part 20 while stator 16 is in its operational position, i.e., when upper part 18 is screwed onto lower part 20 so that lower edge 40 of inner surface 34 is in contact with upper edge 42 of inner surface 36. An alternate conventional means for heating stator 16 would be to apply an electric disc-type heater to the lower surface 76 of lower part 20 while stator 16 is in its operational position. The temperature of the stator 16 can be monitored by any conventional thermocouple probe 78 inserted into thermocouple well 80. Also, if it were desired to cool the rheometer rapidly after the material was tested therein, appropriate known cooling means applied externally and/or internally to said rheometer could be used to achieve this result. The above described thermocouples could be used to monitor the temperature of said rheometer as it is being cooled.

When the entire coaxial cylinder rheometer 10 reaches a uniform desired temperature, upper part 18 is unscrewed from lower part 20 and removed therefrom. The material, which may be in many known forms, e.g., pellet, powder, flake, chip, fiber, etc., and which is to be charged into gap 12 is placed in the trough-like ring 82. This trough-like ring 82 is generally a concave, annular shaped reservoir. Trough-like ring 82 is located in upper surface 84 which is located between inner surface 36 and surface 46 and is substantially normal to inner surface 38 of stator cavity 22. The upper part 18 is then replaced onto lower part 20 and screwed down onto lower part 20 until the projection-like ring 86 comes into contact with the material deposited in trough-like ring 82. The projection-like ring 86 is generally an annular embossment shaped and positioned to fit into said reservoir 82. Projection-like ring 86 is located on the surface 88 which is located between inner surface 34 and surface 44 and is substantially normal to inner surface 38 of stator cavity 22.

The trough-like ring 82 is designed so that its volume is several times that of gap 12 in order to accommodate deposited material having a low (less than 0.5 gram/cubic centimeter) bulk density. The trough-like ring serves as a repository for the deposited material as said material is heated and changes from its deposited state to a flowable state. As the deposited material becomes flowable, the upper part 18 is further screwed onto the lower part 20 so that the projection-like ring 86 continues into the trough-like ring 82 and, therefore, starts to extrude said material from the trough-like ring 82 through passageway 90 into gap 12. The form of both the trough-like ring 82 and the projection-like ring 86 is that of approximately one half a toroid and the cross-sectional area of said projection-like ring is approximately equal to but no greater than the cross-sectional area of said trough-like ring.

As the upper part is screwed onto the lower part so that said two parts move together into their aforesaid operational position, simultaneously the projection-like ring 86 extends fully into the trough-like ring 82 extruding the flowable material therebetween through passageway 90 into gap 12 and the lower edge 40 of inner surface 34 comes into contact with the upper edge 42 of inner surface 36 to form a complete and uninterrupted inner surface 38 of stator cavity 22. Said material having been charged into gap 12, said drive means 58 can now be activated to move said rotor in a desired mode of operation for testing the rheological properties of said material.

An alternative embodiment of the two-part stator of this invention is set forth in FIG. 2. The operation of this particular embodiment is the same as the operation of the preferred embodiment above described but the configuration of the upper and lower parts of said stator have been changed. Therefore, the operation of this embodiment will not be reiterated and primarily only those stator parts which have a changed configuration will be labeled and described. These parts will be designated with the same numbers used for corresponding parts in FIG. 1 but with a prime superscript.

18' represents the upper part and 20' represents the lower part of stator 16'. 26' is the bolt hole through flange 28' for fastening lower part 20' to any conventional and desired surface. 30' represents the screw threads and 48' represents the pilot surface of surface 44'. 32' represents the screw threads and 50' represents the pilot surface of surface 46'. In this embodiment, surface 54' is the same as surface 44'.

Another alternative embodiment of the two-part stator of this invention is set forth in FIG. 3. Again, the operation of this particular embodiment is the same as the operation above described for the preferred embodiment but the configuration of the upper and lower parts of said stator have been changed. Hence, the operation of this embodiment will not be repeated and basically only those parts of the stator which have a changed configuration will be labeled and described. These parts will be designated with the same numbers used for corresponding parts in FIG. 1 but with a double prime superscript.

18" is the upper part and 20" is the lower part of stator 16". 26" represents the bolt hole through lower part 20' since this particular configuration has no flange such as that designated 28 in FIG. 1. The bolt or screw which passes through hole 26" would fasten into any conventional and desired surface. 30" represents the screw threads and 48" represents the pilot surface of surface 44". 32" represents the screw threads and 50" represents the pilot surface of surface 46". Surface 54" represents the outermost surface of upper part 18".

Having described my invention, it will become obvious to one skilled in the art that other configurations and functional means could be used to achieve the ends of this invention without departing from the spirit of this invention. The true scope of this invention is encompassed in the following claims.

What is claimed is:

1. In a rheometer having a cylindrical stator with a cavity therein and a rotatable cylindrical rotor concentrically positioned within said cavity and with a space therebetween, heating means supplying heat to said stator, the improvement comprising said stator being formed of two parts having
    a. a cylindrical bottom part having a concave, annular reservoir in the surface thereof which abuts with the second part of said stator, and
    b. a cylindrical top part having an annular embossment on the surface thereof which abuts with said aforesaid reservoir containing surface of said bottom stator part, said embossment shaped and positioned to fit into said reservoir, means for axially moving said top and bottom parts into abutting relationship at the aforesaid surfaces with said embossment and reservoir moved together, and passageway means connecting said reservoir and said space between said stator and rotor such that molten material extrudes from said reservoir into the space between the stator and rotor when said embossment and reservoir are moved together.

2. The improvement of claim 1 wherein said concave, annular reservoir has the form of approximately ½ a toroid.

3. The improvement of claim 2 wherein said annular embossment has the form of approximately ½ a toroid.

4. The improvement of claim 3 wherein the cross-sectional area of said annular embossment is approximately equal to but no greater than the cross sectional area of said concave, annular reservoir.

5. The improvement of claim 1 wherein the means for axially moving said top and bottom parts comprises a screw-type means.

6. The improvement of claim 5 wherein said screw-type means comprises mating screw threads on said top and bottom parts such that said threaded parts can be screwed together and apart.

7. A rheometer adapted to indicate the rheological properties of highly viscous and/or thermally sensitive materials, said rheometer having a cylindrical stator element, a cylindrical rotor element concentrically positioned within said stator element, said rotor element being capable of axial and rotational movement, means for heating said stator element and said rotor element, means for sensing the temperature of said stator element and said rotor element, a gap between the outer surface of said rotor element and the inner surface of said stator element, means for moving said rotor element relative to said stator element, means for measuring the parameters of movement of said rotor element, wherein the improvement comprises a two-part cylindrical stator element having an upper part and a lower part, said upper part having an inner surface parallel to the axis of said stator element, an other surface spaced radially outward from said inner surface and parallel thereto, and a lower surface between said inner surface and said other surface and substantially normal to said inner surface, said lower part having an inner surface parallel to the axis of said stator element, an other surface spaced radially outward from said inner surface and parallel thereto, and an upper surface between said inner surface and said other surface and substantially normal to said inner surface, means for connecting the upper part to the lower part so that the inner surface of said upper part is axially aligned with the inner surface of said lower part, the upper part having a projection-like ring on the lower surface thereof, the lower part having a trough-like ring in the upper surface thereof for receiving said projection-like ring which is aligned with said trough-like ring, said trough-like ring being used as a depository for the material to be tested while said material is changing from its deposited state to a flowable state, said connecting means being capable of moving said lower part and said upper part together into an operational position wherein simultaneously said projection-like ring moves into said trough-like ring and extrudes the flowable material therebetween through a passageway means into the gap between said rotor and said stator and the bottom edge of the inner surface of the upper part moves into contact with the top edge of the inner surface of the lower part to form a complete and uninterrupted stator inner surface and said connecting means also being capable of moving said upper part and said lower part apart out of said operational position.

8. The improvement of claim 7 wherein said other surface of said upper part comprises an intermediate surface and said other surface of said lower part comprises an intermediate surface.

9. The improvement of claim 7 wherein said other surface of said upper part comprises an outer surface and said other surface of said lower part comprises an intermediate surface.

10. The improvement of claim 7 wherein said other surface of said upper part comprises an intermediate surface and said other surface of said lower part comprises an outer surface.

11. A rheometer adapted to indicate the rheological properties of highly viscous and/or thermally sensitive material, said rheometer having a cylindrical stator element with a cavity therein, a cylindrical rotor element concentrically positioned within the cavity of the stator element, means for moving said rotor element relative said stator element in either axial or rotational movement, means for measuring the parameters of movement of said rotor element, means for controlling the heating of both said stator element and said rotor element, said rotor element being sized relative the cavity of the stator element to provide a gap between the outer surface of said rotor element and the inner surface of said stator element, the improvement comprising making said stator element in two parts, an upper part and a lower part, said cavity extending through both parts, means for moving said upper part and said lower part together into an operational position and apart out of said operational position, when said two parts are together in said operational position, the inner surface of the upper part and the inner surface of the lower part form a complete and uninterrupted stator inner surface, on the surfaces of the upper and lower parts which surfaces move together into abutting relationship in said operational position and outwardly from the inner surface of both parts, there being positioned on one part a projection-like ring and on the other part a trough-like ring for receiving said projection-like ring, whereby said trough-like ring being used as a repository for the material to be tested while said material is changing from its deposited state to a flowable state, said upper and lower parts moving together into said operational position whereby said projection-like ring moves into said trough-like ring and extrudes the flowable material therebetween through a passageway means into the gap between said rotor and said stator with said measuring of parameters taking place after the two parts have moved together into said operational position to form a complete and uninterrupted stator inner surface.

* * * * *